United States Patent [19]

Lee et al.

[11] 4,428,403

[45] Jan. 31, 1984

[54] CONDUIT HAVING SPIRALLY WOUND MONOFILAMENT MATERIAL

[75] Inventors: Kyu H. Lee, King of Prussia; Christopher H. Porter, Newtown Square, both of Pa.

[73] Assignee: Extracorporeal Medical Specialties, Inc., King of Prussia, Pa.

[21] Appl. No.: 385,178

[22] Filed: Jun. 4, 1982

Related U.S. Application Data

[63] Continuation of Ser. No. 218,340, Dec. 19, 1980, abandoned.

[51] Int. Cl.³ .............................................. F16L 11/12
[52] U.S. Cl. .................................... 138/130; 138/123; 138/153; 138/172; 138/177; 138/178; 138/38; 138/DIG. 6; 165/133; 165/156; 165/184; 422/46; 422/47
[58] Field of Search ................. 138/38, 111, 112, 113, 138/114, 118, 122, 130, 144, 129, 123, 153, 177, 178, DIG. 8; 165/162, 156, 163, 165, 179, 181, 184, 133; 422/46, 47

[56] References Cited

U.S. PATENT DOCUMENTS

| 644,841 | 3/1900 | Allen | 165/156 X |
|---|---|---|---|
| 1,777,356 | 10/1930 | Fisher | 165/163 X |
| 2,693,346 | 11/1954 | Petersen | 165/163 |
| 4,065,264 | 12/1977 | Lenin | 165/163 X |
| 4,116,270 | 9/1978 | Marushkin et al. | 165/163 X |
| 4,316,501 | 2/1982 | Bowden et al. | 165/163 X |

Primary Examiner—James E. Bryant, III
Attorney, Agent, or Firm—Lawrence D. Schuler

[57] ABSTRACT

Device useful as a heat exchanger for blood or as an apparatus in which blood may be treated or reacted with selected reactants. Device comprises hollow tubing which has plastic monofilament placed in a generally spiral configuration around its outer surface, said monofilament being in the form of continuous or discontinuous projections or ridges. Strands of wire may be substituted for the plastic monofilament. Hollow tubing having such plastic monofilament or strands of wire is also included.

4 Claims, 7 Drawing Figures

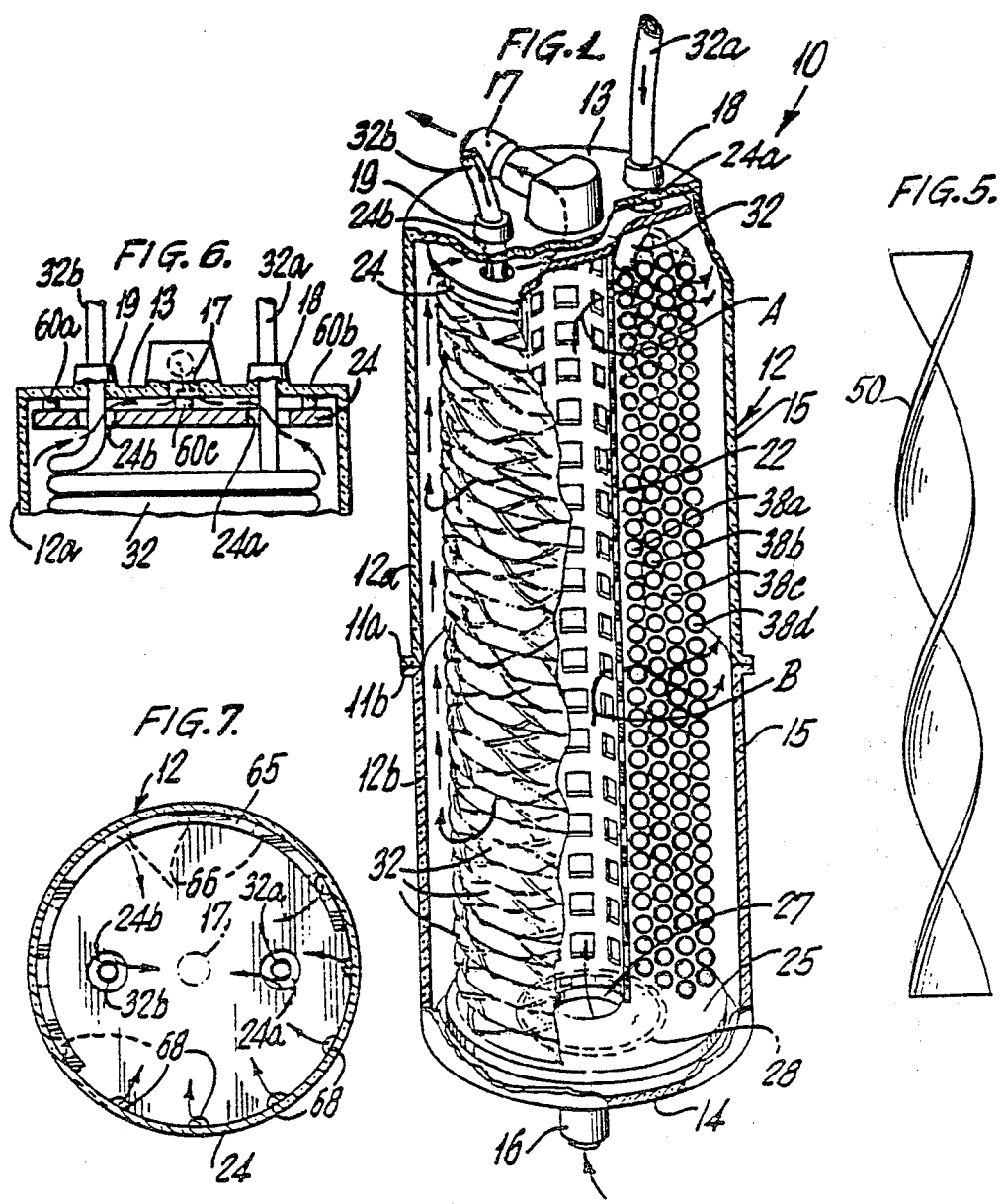

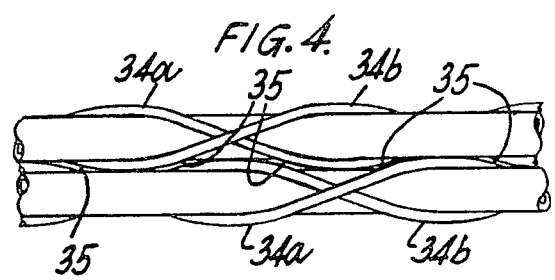
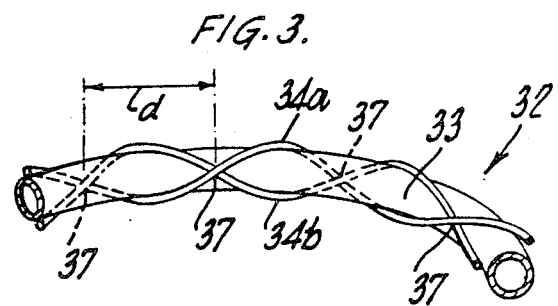
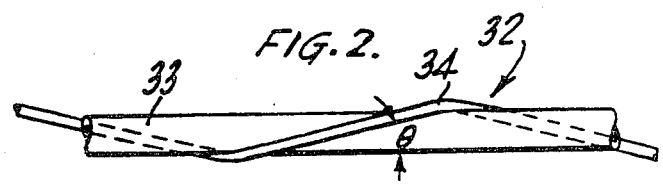

CONDUIT HAVING SPIRALLY WOUND MONOFILAMENT MATERIAL

This is a continuation of application Ser. No. 218,340, filed Dec. 19, 1980, now abandoned.

FIELD OF THE INVENTION

This invention relates to devices useful in the treatment of blood or similar biological fluids. More particularly, this invention relates to a device which can serve as a heat exchanger for blood or which can be used as a reactor in which blood is reacted with selected reactants or which can serve both of these purposes simultaneously.

BACKGROUND OF THE INVENTION

Current medical treatment frequently involves the extra-corporeal treatment of blood, that is, blood is removed from a patient's body, treated, and then returned to the patient. Thus, for example, during the course of open heart surgery, blood is removed from a patient, oxygenated in a suitable oxygenating device, and returned to the patient. In the case of kidney mulfunction or failure, blood is removed and treated, for example, in a dialyzer to remove toxic metabolites. The purified blood is then returned to the patient.

In the above or other instances, it may be necessary or desirable to add certain additives to the blood. For example, where blood is being dialyzed or oxygenated, heparin or a similar anticoagulant may be added to the blood after it has been withdrawn from the patient and before it is dialyzed or oxygenated.

In still other instances, it may be desirable to add reactants to the blood after it has been taken from a patient in order to achieve a desired medical effect. For example, it has been proposed to treat sickle cell anemia by a process which includes reacting a patient's blood with cyanate ion in a suitable extracorporeal device. See Vol. XX, *Transactions of the American Society of Artificial Internal Organs,* page 574 (1974).

In extracorporeal treatments, such as those mentioned above, the temperature of the blood taken from the patients corresponds to the patient's body temperature which, in normal circumstances, is about 98.6° F. The extracorporeal environment to which the removed blood is exposed has a temperature which is considerably lower, usually about 68° F. to 72° F. Heat exchangers may be employed in such instances in order to insure that blood returned to the patient has the desired temperature. Heat exchangers are also employed in extracorporeal blood circuits where it is desired to either raise or lower the temperature of the blood after it has been withdrawn from the patient and prior to its treatment or reaction thereof.

SUMMARY OF THE INVENTION

In accordance with the present invention, there is provided a device useful in the extracorporeal treatment of blood. The device comprises a casing having a hollow interior, a first inlet means, a first outlet means, a second inlet means, and a second outlet means, a perforated hollow core secured within said casing, the interior of said core being in fluid communication with said first inlet means, and a length of hollow tubing having a first end and a second end, the first end of the tubing being connected to said second inlet means and the second end of said tubing being connected to said second outlet, said tubing having spacing means on the outer surface thereof, said tubing being coiled around the outside of said core and within said casing.

BRIEF DESCRIPTION OF THE DRAWINGS

The invention will be more clearly understood with reference to the following detailed description and with reference to the appended drawings in which:

FIG. 1 is a view, with some parts in cross-section and other parts broken away, of a device in accordance with the present invention;

FIG. 2 is a fragmentary view of one kind of tubing which can be used in the device of FIG. 1;

FIG. 3 is a fragmentary view of another kind of tubing which can be used in the device of FIG. 1;

FIG. 4 is a fragmentary view showing how two portions of the tubing of FIG. 2 are arranged with respect to one another in the device.

FIG. 5 is a view of a fluid spreading means which may be used in the device of FIG. 1; and FIGS. 6 and 7 are detail views of a portion of the device of FIG. 1.

DESCRIPTION OF THE PREFERRED EMBODIMENT

Referring now to FIG. 1 of the appended drawings, there is shown device 10 in accordance with the present invention. Device 10 comprises an elongated, cylindrical hollow casing 12, an elongated, cylindrical perforated hollow core 22 generally centrally located within casing 12, and hollow tubing 32 wrapped in coil form around core 22.

Hollow casing 12 is formed from two open-ended cylinders 12a, 12b. Each such cylinder comprises a closed end portion and a cylindrical wall portion and each has a small flange, 11a and 11b respectively, at its open end. The two cylinders are joined at their flanges by ultrasonic welding or with a suitable adhesive to give a leakproof seal. The resulting hollow casing 12 comprises a first or top end portion 13, a second or bottom end portion 14, and a generally cylindrical side wall 15. The hollow casing has a first inlet means 16 in the bottom thereof and a first outlet means 17 in the top thereof. In addition, casing 12 has a second inlet means 18 and a second outlet means 19 which, in the preferred embodiment, are located in top end 13. The various outlets are connected in fluid tight relationship to casing 12. Preferably, the casing and outlets are made from polystyrene; other materials of construction, such as polycarbonate, may be substituted.

In the preferred embodiment, hollow core 22 is substantially smaller in diameter than casing 12 and has a series of square shaped apertures 24. These apertures are substantially uniform in size, each measuring about 0.2 inch by 0.2 inch and having an area of about 0.04 inch$^2$. Apertures 24 occupy about 50% of the surface area of the outer cylindrical wall of core 22. Other aperture shapes such as rectangular, circular, oval, diamond, triangular, etc. are also suitable.

Hollow core 22 further comprises a top flange 24 and a bottom flange 25, each of which is circular and sized so as to fit within casing 12. Flange 25 has an opening 27 therein which is in fluid communication with the interior of core 22 and the interior of inlet 16. Flanges 24, 25 are sealed to the ends of the core with, for example, an epoxy resin adhesive.

A gasket in the form of O-ring 28 is placed between the bottom surface of flange 25 and the inner surface of bottom end 14 of the casing to form a fluid tight seal. The O-ring, which has a diameter somewhat larger than the diameter of opening 27 in flange 25, can be made from silicone rubber or the like. Alternatively, adhesive may be substituted for the O-ring, such adhesive serving not only as a gasketing material but also as means for securing core 22 within casing 12. Flange 24 is generally circular and has openings 24a and 24b therein. There is a substantially uniform clearance of about 0.06 inch between the periphery of flange 24 and the inside surface of cylindrical wall 15. As will be seen, this clearance, along with openings 24a, 24b, provides a path for fluid to reach first outlet 17 at the top of the device.

Referring now to FIGS. 2-4 of the drawings, hollow tubing 32 comprises ordinary tubing 33 having spacing means 34 on its outer surface. These spacing means minimize the degree of contact between adjacent sections or portions of tubing when it is wrapped around core 22 and to provide openings 35 for passage of a fluid such as a heat exchange medium. The spacing means comprise a ridge or projection of material placed in a winding pattern on the outer surface of tubing 33. This ridge or projection of material may be either continuous or discontinuous. As seen in FIG. 2, the spacing means 34 comprise a continuous length of monofilament which is wrapped in a generally spiral fashion around the outer surface of a length of ordinary tubing 33. Monofilament 34 preferably comprises nylon having an outside diameter of 0.029 inch. Strands of wire such as stainless steel or monofilament of other common plastic materials may be substituted for the nylon monofilament. Tubing 33 must have sufficient flexibility to be formed into a coiled configuration and enough strength to withstand the pressure of fluids flowing therethrough. Tubing 33 is preferably made of polyvinyl chloride, but other material such as stainless steel, polyethylene or silicone rubber could also be used. Tubing 33 having an inside diameter of about 0.2 inch and an outside diameter of about 0.27 inch has been found suitable for use in device 10. Tubings having various dimensions may be employed; however, the inside diameter of the tubing should not be less than about 0.01 inch nor greater than about 1 inch.

Referring to FIG. 2, the angle $\theta$ at which the longitudinal axis of the monofilament intersects the longitudinal axis of tubing 33 may range from about 10° to about 80°. It is preferable, however, that this angle range from about 20° to 70° and even more preferably, the angle $\theta$ should range from about 35° to about 65°. Although tubing comprising a single length of monofilament may be used, it is preferred, as illustrated in FIG. 3, that tubing 32 comprise two lengths of monofilament, 34a, 34b, wrapped around tubing 33, the monofilaments being wrapped in opposite directions to give two continuous ridges of material having cross-over points 37.

As a non-limitative illustration, it has been found that a satisfactory embodiment of tubing 32 can be made by spirally wrapping tubing 33 having an outside diameter of about 0.27 inch with two individual monofilaments of nylon having an outside diameter of about 0.029, so that angle $\theta$ between the longitudinal axis of either of the monofilaments and the longitudinal axis of the tubing is about 49°. The additional advantage (aside from its spacing function) to be derived from tubing 32 illustrated in FIG. 3 are twofold. First, the two monofilaments are frictionally engaged at their crossover points 37 and this helps prevent slippage of the monofilaments which might otherwise occur. Second, the crossover points 37 provide a "double thickness" of spacing material.

Variations of the structure shown in FIG. 3 will be obvious to those skilled in the art. Additional lengths of monofilament, e.g., three or more could be employed. Additionally, two monofilaments could be wound around tubing 33 in the same direction in spaced apart relationship. The latter mentioned structure does not have the additional advantage mentioned in the foregoing paragraph, but is nonetheless suitable for use in the invention. Where two or more monofilaments are used, their respective axes may make different angles $\theta$ with the longitudinal axis of the tubing 33. It will be apparent that the spacing, d, between adjacent crossover points 37 will be a function of the outside diameter of tubing 33 and the angle(s) at which the monofilaments are wrapped therearound.

The spacing means comprising the projections or ridges of material on the outer surface of the tubing can be formed by means other than wrapping with a length of plastic monofilament. For example, stainless steel or similar wire or other kinds of plastic may be substituted for the aforementioned nylon monofilament. Alternatively, the projections or ridges on the outer surface of the tubing can be provided during the manufacturing operation by extruding a base material, e.g., polyvinyl chloride, through a die whose configuration corresponds to the configuration desired for the tubing. In addition, projections 34 need not take the continuous form such as that obtained by wrapping with a length of monofilament material, but may be discontinuous. For example, the desired projections may comprise a plurality of discrete individual peaks of material arranged on the outer surface of the tubing. Such individual peaks of material may be provided in the form of e.g., cones, cones with truncated tops, pyramids, spheres, etc. The important thing is that there be at least one course of projections or ridges of material around the tubing.

As can be seen in FIG. 1, tubing 32 is wound around core 22 is spiral fashion to provide four layers 38a, 38b, 38c, 38d of turns lying outwardly in the radial direction from core 22 toward the inner wall of casing 12. A fewer or greater number of layers may be employed depending upon such factors as the size of the casing, the size of the tubing, the desired hold-up volume, etc. End portions 32a, 32b of tubing 32 are conveniently arranged in device 10 to extend through openings 24a and 24b, respectively, in flange 24. End portion 32a of tubing 32 is secured in fluid tight relationship to second inlet means 18, while end portion 32b of the tubing is secured in fluid tight relationship to second outlet means 19. Openings 24a and 24b are desirably larger than tubing 32 so that the aforementioned paths for the flow of liquid will be maintained. In operation of device 10, fluid may enter end portion 32a, flow through coiled tubing 32, and exit therefrom at end portion 32b.

Where core 22 has not been otherwise secured within casing 12, for example, by applying a suitable adhesive between flange 25 and bottom end 14 of the casing, it is desirable to insert a spacer element between flange 24 and top end 13 of the casing. The spacer element must be such that fluid may flow, as indicated by the directional arrows at the left side of FIG. 1, in unimpeded fashion upwardly in the space between the outermost layer of tubing 32 and cylindrical wall 15, over the upper surface of flange 24, and out of the device through first outlet means 17. As illustrated in FIG. 6, the spacer element may comprise three small pieces 60a, 60b, 60c of solid plastic material placed between flange 24 and end wall 13, the pieces being arranged in a spaced-apart triangular relationship with respect to one another. These pieces of plastic are sized so that when they are in place, they urge core 22 against, and cause compression of, compressible O-ring 28. Core 22 is thus secured within casing 12. Simultaneously, O-ring 28 is brought into engagement with the bottom surface of flange 25 and the inner surface of bottom wall 24, thus allowing fluid to flow directly through inlet 16 into the interior of core 22 and preventing undesirable radial flow of fluid between flange 25 and the bottom wall 14 of the casing.

Another spacer arrangement is shown in FIG. 7. Flange 24 comprises a series of notches 68 cut into its outer periphery. The spacer element comprises a circular spacer ring 65 having a series of holes 66 therein. When assembling the device, spacer ring 65 is placed between flange 24 and top end 13, and holes 65 in the spacer are aligned with notches 68 in the flange to provide flow paths designated by the arrows in FIG. 7. When flow paths are provided by the arrangement shown in FIG. 7, it is not necessary to have a clearance between the outer periphery of flange 24 and the inner wall of the casing. Thus, it is possible in this instance for the diameter of flange 24 to be substantially the same as the inside diameter of casing 12. Those skilled in the art will recognize that the presence of flange 24 on core 22 is not critical to the invention. Device 10 will function as desired even if core 22 does not comprise flange 24.

FIG. 5 illustrates a fluid spreading means 50 which can be inserted into the interior of core 22 to achieve a more uniform distribution of the fluid flowing through the core. The fluid spreading means 50 comprises an elongated strip of metal or plastic, e.g., polycarbonate, twisted around its longitudinal axis. Suitably, each three inch section of the elongated strip has a full 360° twist. The twisted strip can be sized so that it fits snugly within core 22.

Device 10 may be used as a heat exchanger for blood as follows: A source of blood, for example, that from a patient, is connected to end portion 32a of tubing 32. End portion 32b is connected to tubing which returns the blood to the patient. A source of heat exchange fluid, e.g., water, heated to the desired temperature is pumped to inlet 16 of the device. The heat exchange fluid flows into the interior of core 22 and rises toward the top thereof. At the same time, the heat exchange fluid flows radially through the apertures in the core wall and contacts the outer surface of tubing 32, thus transferring heat to the blood. The heat exchange fluid flows through the spaces 35 between the turns and layers of tubing 32. The arrows designated A and B in FIG. 1 illustrate typical paths taken by the heat exchange fluid when the device is in operation. The heat exchange fluid, after flowing radially through the turns and layers of tubing, flows upwardly in the space between the outermost layer of tubing 32 and the wall of the casing. The fluid then flows through the space between the casing wall and the periphery of the flange. Additionally, or alternatively, the heat exchange fluid can flow through openings 24a, 24b in flange 24. Once the fluid reaches the upper surface of flange 24 it flows out of device 10 by way of outlet 17 and is returned to the pump for recirculation.

The device may simultaneously be used as a heat exchanger and as an apparatus wherein blood is mixed and/or reacted with other materials. Heparin, for example, may be introduced via a suitable inlet port (not shown) upstream of blood inlet 32a. Mixing of the blood and heparin will be effected in the coiled portions of tubing 32. As another example, a desired quantity of a solution of potassium cyanate may be added upstream of the blood inlet. Reaction of the hemoglobin in the blood with the cyanate ion occurs in the spiral portion of tubing 32, the rate and extent of the reaction being influenced by, among other factors, the temperature to which the blood is heated while circulating within tubing 32 and the hold-up volume defined by that tubing.

It will be recognized that the blood hold-up volume will be defined by both the internal diameter of tubing 32 and the total length of tubing used and that the blood hold-up volume may be selected to suit various circumstances.

As an alternative structure, it is possible to size flange 24 so that its diameter corresponds substantially to the inside diameter of casing 12. In such event, openings 24a, 24b would provide flow paths by which the fluid flowing in casing 12 can reach outlet 17. Additional openings, corresponding generally to openings 24a, 24b, may be provided if necessary. Alternatively or additionally, notches may be cut into the periphery of flange 24 to provide paths for fluid flow. Thus, it will be appreciated that flange 24, either because it has a diameter which is smaller than the inside diameter of casing 12, or because it comprises the aforementioned openings such as 24a, 24b, or because it comprises notches cut into its periphery, defines at least in part the flow path by which fluid flowing in casing 12 reaches first outlet means 17.

It will also be understood that, while perhaps less desirable, it is possible to run the heat exchange fluid through tubing 32 and to run the blood or like material to be heated over the outer surfaces of that tubing. In addition, it is possible to have the heat exchange fluid flow enter the device through "outlet" 17 and exit the device through "inlet" 16. Finally, it will be understood that all materials which will be contacted by blood must be non-toxic and non-thrombogenic.

We claim:

1. Conduit useful, for example, in a heat exchange device or in a device for the treatment of blood, said conduit consisting essentially of hollow tubing and at least two continuous lengths of monofilament material, said hollow tubing consisting essentially of a flexible polymeric material and having substantially constant inside and outside diameters and a continuous lumen extending the length thereof, one of said lengths of monofilament material being wrapped in a generally spiral configuration around the outer surface of said tubing in a first direction, another of said lengths of monofilament material being wrapped in a generally spiral configuration around the outer surface of said tubing in a direction opposite said first direction to thereby provide crossover points at which said two lengths of monofilament material are frictionally engaged, said conduit being formed into a coil in which the degree of contact between adjacent sections of said tubing is minimized and in which there are spaces for the flow of a fluid over the outer surfaces of said tubing.

2. Conduit according to claim 1 wherein said hollow tubing comprises a material selected from the group consisting of polyvinyl chloride, polyethylene and silicone rubber, and said two lengths of monofilament material are made of nylon.

3. Conduit according to claim 1 wherein said hollow tubing is polyvinyl chloride tubing whose inside diameter is not less than about 0.01 inch nor more than about one inch, said two lengths of monofilament material have an outside diameter of about 0.029 inch, and the angle between the longitudinal axis of said tubing and the longitudinal axis of either of said two lengths of continuous monofilament material is about 49°.

4. Conduit according to claim 3 wherein said hollow tubing has an inside diameter of about 0.01 inch and an outside diameter of about 0.27 inch.

* * * * *